US005662096A

United States Patent [19]
Walters

[11] Patent Number: 5,662,096
[45] Date of Patent: Sep. 2, 1997

[54] TRIGGER TO ACTIVATE SUPERCOOLED AQUEOUS SALT SOLUTION FOR USE IN A HEAT PACK

[75] Inventor: Dale E. Walters, St. Louis, Mo.

[73] Assignee: Omni Therm, Inc., St. Louis, Mo.

[21] Appl. No.: 497,826

[22] Filed: Jul. 3, 1995

[51] Int. Cl.⁶ ..................................... A61F 7/00
[52] U.S. Cl. .................. 126/263.03; 126/263.08
[58] Field of Search .............. 126/263.03, 263.04, 126/263.08

[56] References Cited

U.S. PATENT DOCUMENTS

| | | |
|---|---|---|
| 1,433,010 | 10/1922 | Hogan . |
| 1,915,523 | 6/1933 | Ferguson . |
| 2,220,777 | 11/1940 | Othmer . |
| 2,289,425 | 7/1942 | Hogan . |
| 3,093,308 | 6/1963 | Snelling . |
| 3,301,250 | 1/1967 | Glasser . |
| 3,951,127 | 4/1976 | Watson et al. . |
| 4,007,390 | 2/1977 | Stanley et al. . |
| 4,106,477 | 8/1978 | Feld . |
| 4,451,383 | 5/1984 | Arrhenius ............ 126/263.03 X |
| 4,488,552 | 12/1984 | McCann et al. . |
| 4,503,838 | 3/1985 | Arrhenius et al. ......... 126/263.03 |
| 4,572,158 | 2/1986 | Fiedler . |
| 5,305,733 | 4/1994 | Walters . |

FOREIGN PATENT DOCUMENTS

| | | | |
|---|---|---|---|
| 2907366 | 9/1980 | Germany | 126/263.03 |
| 401312356 | 12/1989 | Japan | 126/263.04 |

Primary Examiner—Carl D. Price
Attorney, Agent, or Firm—Kalish & Gilster

[57] ABSTRACT

A trigger to initiate crystallization of a supercooled aqueous salt solution of a heat pack, thereby liberating heat. The trigger, when activated, pierces the container, allowing the salt solution to contact salt crystals, and initiate crystallization of the solution. A seal over the trigger prevents the solution from leaking from the heat pack. Optionally, the heat pack contains a flexible foam rubber pad immersed in the salt solution in the container to prevent saddlebagging.

17 Claims, 3 Drawing Sheets

TRIGGER TO ACTIVATE SUPERCOOLED AQUEOUS SALT SOLUTION FOR USE IN A HEAT PACK

FIELD OF THE INVENTION

This invention relates to heat packs, and more particularly to such a heat pack in the form of a heating wherein a supercooled aqueous salt solution is activated by a trigger to produce heat. The solution is encased in a flexible container, and the trigger is affixed to the flexible container. Crystallization is initiated when the trigger is activated, and heat is thereby liberated. An optional foam pad is submerged in the salt solution in the container to alleviate the problem of saddlebagging when the heating pad is applied to the human body.

BACKGROUND OF THE INVENTION

Heat packs utilizing supercooled aqueous salt solutions have been used for some time for the treatment of soreness of muscles of athletes and sportsman in localized areas. From the simple hot water bottle we have progressed upward to the use of supercooled aqueous salt solutions wherein the temperatures can be controlled as well as the duration of the heat given off. Various solutions such as sodium acetate and calcium nitrate tetrahydrate are examples of such solutions.

Various techniques of initiating crystallization have been recommended, including inserting a crystal of material into the supercooled solution, and scraping some metal inside the container to introduce impurities into the supercooled solution. Examples of these techniques are disclosed in the following U.S. Pat. Nos. 1,433,010; 2,289,425; 2,220,777; 3,093,308; 4,077,390; and 4,572,158. U.S. Pat. No. 1,915,523 discloses the introduction of air into the solution by means of a valve. This complicated method involves the use of both hands to manipulate the valve.

U.S. Pat. No. 5,305,733 discloses a trigger for a heat pack. The trigger pierces a flexible container filled with a supercooled salt solution, wherein the trigger has a piercing means and a sealing means. The trigger allows air to be admitted, initiating precipitation and causing the pack to exotherm.

A variety of techniques have also been directed to the problem of saddlebagging when the heat pack is in use. U.S. Pat. No. 3,301,250 discloses a heat pack that uses vermiculite, iron particles, ammonium chloride, wetting agent and water to provide such a pack. When air is admitted to the mixture, the iron filings oxidize and thereby produce heat. This fairly complicated mixture provides a lumpy heat pack.

U.S. Pat. No. 3,951,127 discloses a flexible heating pack that contains a foam insulation as an external layer to the exotherming chemicals. The foam does not come in contact with the supercooled salt solution.

U.S. Pat. No. 4,106,477 discloses a water activated therapeutic moist heat pad having outer porous water retaining layers which enclose an inner layer of distributed heat generating cells and an associated water retaining absorbent inner porous layer. The inner layers are covered by an outer sponge-like layer to form a composite pad structure capable of retaining a sufficient amount of water for the transfer of heat. The device described is an that of a heat pack using electrochemical cells provided with discrete electrically located shorts to generate internal heating of the cell when it is activated by the addition of water. This device is far more complicated than that claim in the present application. It fails to address the problem of saddlebagging that is remedied in the present invention.

The present invention provides a simple device that is easily manufactured and the trigger is easily activated. Of particular advantage is that the heat pack of the present invention can be initiated using one hand. Of further advantage is that a temperature indicator can be attached to the heat pack to indicate the appropriate temperature. A final advantage is that the heat pack optionally contains a foam rubber pad inside the flexible container which provides additional support, and prevents saddlebagging when the pack is in use. This option is particularly useful in larger heat packs which can be used to place premature babies on and to warm them.

SUMMARY OF THE INVENTION

The present invention relates to a trigger to initiate crystallization of a supercooled aqueous salt solution encased in a flexible container, said trigger comprising a crystalline salt, a puncturing means and a sealing means, wherein the trigger is attached by a sealing means to the exterior of the flexible container, wherein the trigger, when activated, punctures the flexible container, and admits the salt solution thereby, which, when it contacts the salt crystals, initiates crystallization, and wherein the sealing means prevents any leakage of the solution from the container. The flexible container, with the claimed trigger and the enclosed supercooled aqueous salt solution forms a heat pack. Optionally, the flexible container also contains a foam rubber pad immersed in the salt solution which serves to provide additional support and prevent saddlebagging when the pack is in use. Of particular use for these packs containing a pad is as warming pads for neonatal babies in hospitals. Smaller versions are useful as baby heel warmers, as used in hospitals to facilitate the sampling of blood by pricking the heel.

BRIEF DESCRIPTION OF THE DRAWINGS

The above advantages may be more clearly understood from the following detailed description and by reference to the drawings.

DETAILED DESCRIPTION OF INVENTIVE EMBODIMENTS

Figure 1:
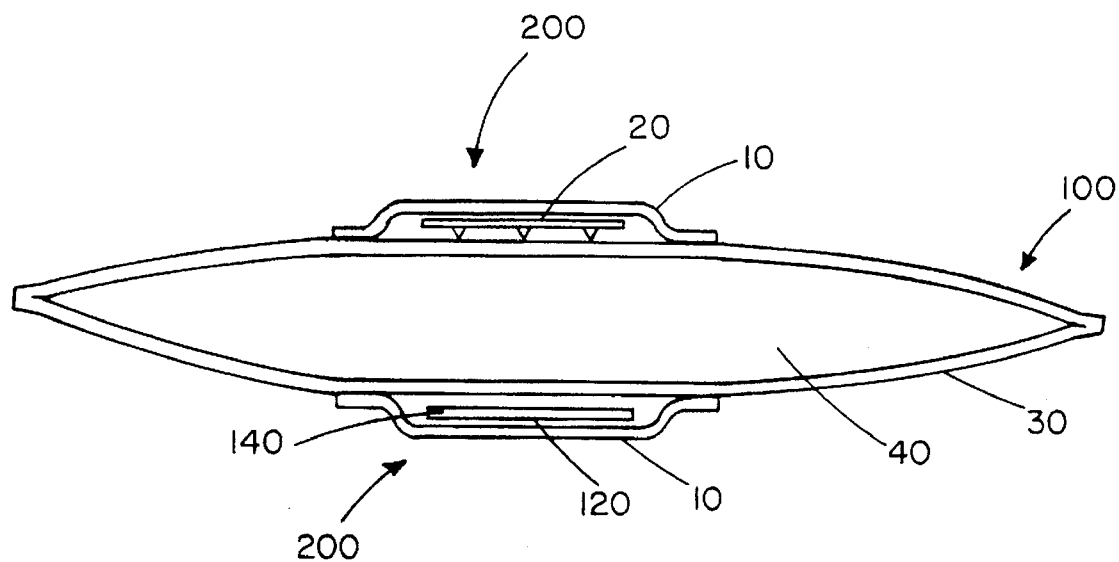
FIG. 1 is a side, sectional view of the heat pack in accordance with the invention, wherein the trigger is not activated.

Referring to FIG. 1, the supercooled salt solution 40 of the present invention relates to supercooled salt solutions, which, when activated, release heat. Suitable solutions include supercooled sodium acetate, lead acetate, calcium nitrate tetrahydrate and sodium thiosulfate. The preferred solution is sodium acetate, which is generally harmless to humans.

The salt solution 40 is made by dissolving the salt in the desired amount of water. The amount of salt to be utilized should permit the salt solution to be supercooled to at least the ambient temperature at which the heat pack is intended to be utilized. Additionally, the amount of salt should not be so great that the resulting solution is activated unintentionally by shaking, etc., when at ambient or use temperature. For example, if a heat pack is to be utilized a 0° C. then the amount of salt used should permit supercooling of the salt solution down to at least that temperature and the solution should be relatively stable at that temperature. However, sufficient salt should be used to enable the supercooled solution to be readily crystallized when the trigger 200 is activated.

The amount of water present in the salt solution will vary depending upon the heat pack temperature desired. As the amount of water increase relative to the amount of salt, the temperature to which the container contents are raised when the salt crystallizes decreases. This means that the maximum temperature of the heat pack 100 can be controlled by appropriate adjustment of the water/salt ratio.

The flexible container 30 of FIG. 1 can be made from any flexible material not affected by the supercooled solution, and impermeable to it. Additionally, the container material must be able to withstand the temperatures (generally on the order of about 60° to 65° C.) to which the heat pack 100 is heated to redissolve the precipitated salt. Suitable materials include plastic materials such as rubber, vinyl, vinyl-coated fabric, nylon polylaminate and polyethylene. Preferably the flexible container is made from nylon polylaminate of a thickness in the range of about 1 mil (0.026 mm) to 10 mils (0.26 mm).

Figure 4:
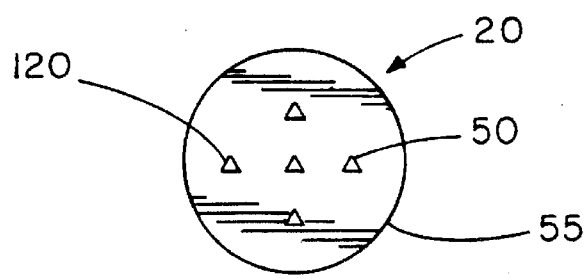
FIG. 4 is a bottom view of the trigger.

The puncturing means 20 is any means suitable for manipulation against the flexible container, thereby puncturing the container and initiating crystallization of the solution. As shown in FIG. 4, examples of suitable puncturing means includes a base plate with a plurality of piercing members 50 protruding from the plate 55. Preferably, the puncturing means constitutes a metal base plate having a plurality of piercing members being constituted by upset portions of the metal base plate. The preferred number of piercing members is in the range of about 3 to 10. The height of the piercing members is preferably in the range of about 10 mil (0.26 mm) to 150 mil (3.9 mm).

As shown in FIG. 4, the plate 55 can be made of such solid materials as hard plastics and metals. Preferably, the plate is made of a ferrous material, such as stainless steel, and formed in a circle. The preferred diameter of the plate is in the range of 0.25 inch (0.635 cm) to 1.5 inch (3.8 cm).

Figure 2A:
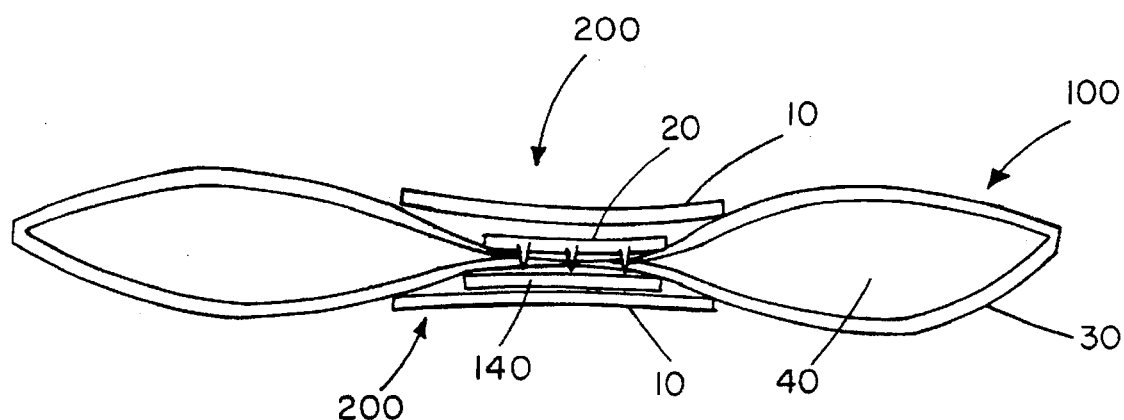
FIG. 2A is a side, sectional view of the heat pack, wherein the trigger is activated, i.e., the trigger has punctured the flexible container.
Figure 5:
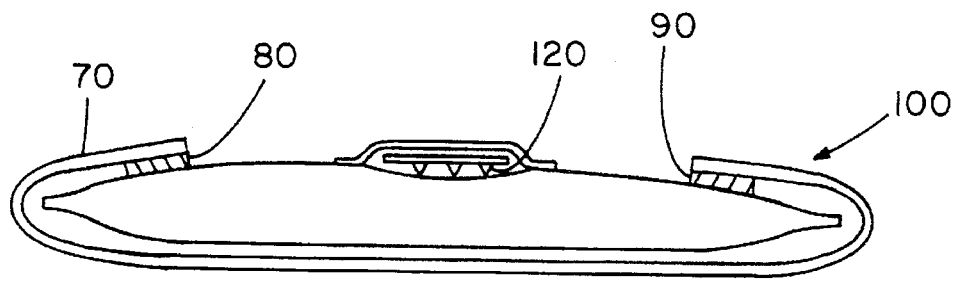
FIG. 5 is a side sectional view of the heat pack with a fastening means, the heat pack being of the type used as an infant heel warmer.
Figure 7:
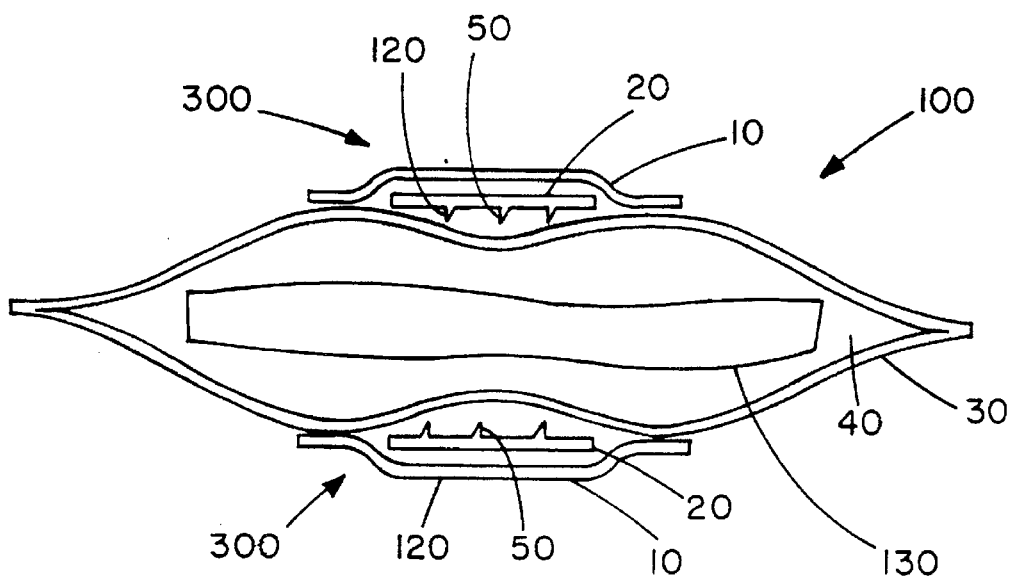
FIG. 7 is a side, sectional view of the a pack of the invention, but wherein the trigger is two puncturing means on opposite sides of the flexible container, wherein the puncturing means have salt crystals deposited on them.

The salt crystals 120 in the trigger 200 can be placed in the trigger by a variety of means. The salt can be crystallized on the piercing members 50 by dipping the piercing members 50 in a supersaturated salt solution and evaporating the solvent. This embodiment of the invention is shown in FIGS. 4, 5 and 7. The salt crystals 120 can be placed in the trigger by sprinkling during the assembly of the trigger. Alternatively, the salt crystals 120 can be deposited on a chip of cardboard or other support means 140 and attached to the flexible container 30 by a sealing means 10, opposite the puncturing means 20. This embodiment is shown in FIGS. 1 and 2A. The salt can be any type of inorganic salt, such as sodium chloride or calcium chloride, but the preferred salt is that of sodium acetate, because of its effectiveness in initiating crystallization in supersaturated solutions of sodium acetate. The preferred chip is in a square or rectangular shape with the length of the sides in the range of 0.25 inch to 1.5 inches.

The sealing means 10 is any means suitable for adhering the puncturing means to the flexible container and preventing the leaking of the solution from the container. Such means includes a contact adhesive strip that covers the puncturing means, securing it against the container, a band encircling the container, or adhesive means applied between the puncturing means and the flexible container. The preferred means is an contact adhesive seal having a diameter greater than that of the trigger plate 55. The diameter of the seal is preferably in the range of 0.75 inches (1.80 cm) to about 2.0 inches (5.08 cm).

Figure 2:
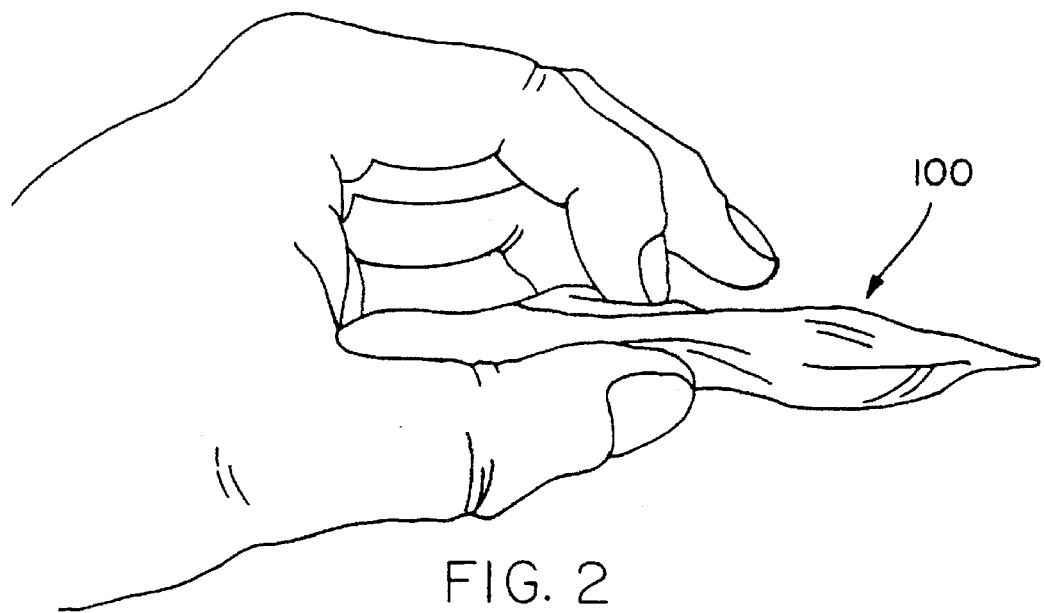
FIG. 2 illustrates manipulation of the heat pack for triggering its operation.

Typical operation is shown in FIG. 2. The user places pouch 30 between the thumb and index finger. Squeezing pressure against the opposite walls causes piercing and resultant activation by triggering of precipitation. One may alternatively rub the thumb nail over the adjacent surface to bring the opposite bag wall in contact with the piercing members.

FIG. 2A shows a side sectional view of the heat pack 100 wherein the trigger has been activated. The trigger is activated by applying pressure to the puncturing means sufficient to puncture the flexible container. Such pressure can be accomplished by compressing the trigger 200 between the thumb and index finger by placing the thumb under the container and the index finger over the trigger. The trigger 200 can also be activated by pressing against the puncturing means 20 while the heat pack is resting on a solid surface. A particular advantage of the present invention is that the heat pack is easily activated with one hand. The piercing members 55 are shown in FIG. 2 as piercing both walls of the flexible container 30 twice, thereby allowing the salt crystals 120 to come in contact with the supercooled salt solution 40, precipitating the salt and initiating heating.

Figure 3:
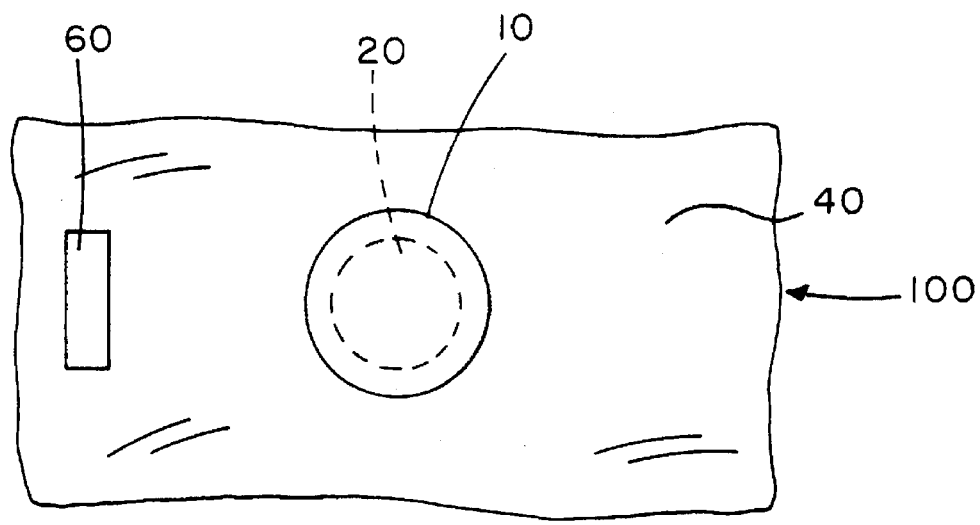
FIG. 3 is a top view of the heat pack.

FIG. 3 shows a top view of the heat pack 100 having a temperature indicator 60 affixed to exterior of the flexible container. The temperature indicator can be any indicator known in the art, preferably a liquid crystal indicator.

The heat pack of the present invention can be sized for being used to heat body parts, such as joints and extremities. In a preferred embodiment, the heat pack is sized for serving as an infant heel warmer. It has a fastening means for securing the heat pack to a body part, such as the ankle or the wrist. The fastening means can be an elastic band, a contact adhesive applied to the bottom surface of the flexible container, or a strip which encircles the body part. The preferred fastening means is a strip which encircles the body part. As shown in FIG. 5, the strip can be adhesively attached to the heat pack 100 by an adhesive means 80. A flexible strap 70 is sufficiently long to encircle a body part, in the range of 2 inches (5.08 cm) to 6 inches (15.24 cm). The strap can be made of plastic or fabric, such as cotton cloth. Preferably, the strap is hypoallergenic, so as to not irritate the skin. At the opposite end of the strap is a contact adhesive 90 that is peeled from the flexible container and reapplied to the heat pack when the body part is encircled.

Figure 6:
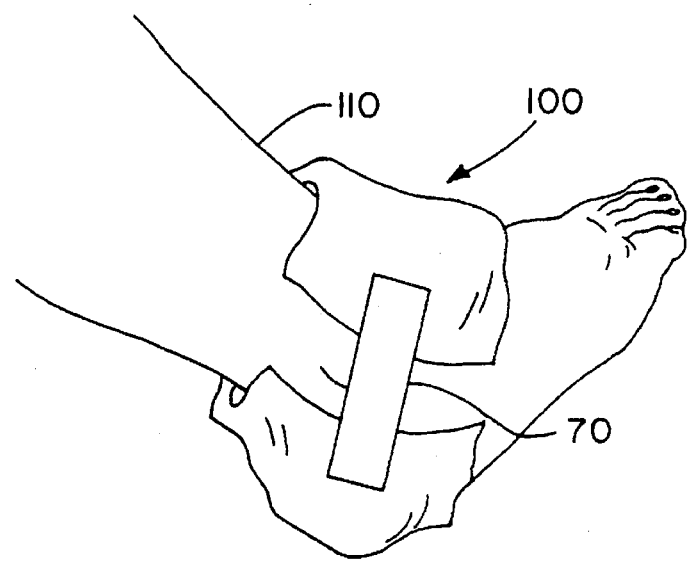
FIG. 6 is a side view of a heat pack of the invention fastened to an ankle, the heat pack being of the type and form in FIG. 5.

In FIG. 6 an ankle 110 is encircled by the heat pack 100, which is fastened by flexible strap 70. The heat pack is held securely against the ankle by the strap, being this unusually advantageous for use of the heat pack as an infant heel warmer.

FIG. 7 discloses a preferred heat pack 100 of larger dimensions, in the order of 10 to 20 inches by 15 to 30 inches, suitable to place an infant on, having a trigger 300 made of two puncturing means 20 on opposite sides of the flexible container 30, wherein the trigger is activated by applying pressure, causing the piercing members 50 to work against each other and puncture the flexible container 30 twice, thereby admitting the salt solution 40 to contact the salt crystals 120, deposited on the piercing members 50 and triggering precipitation of the salt.

Within the flexible container 30 is a foam rubber pad 130. The foam pad is typically of the same shape and size of the flexible container 30, e.g., rectangular, but slightly smaller so as to fit within the container without buckling or wrinkling. Various synthetic poromers, i.e., foam materials, would be appropriate, but preferred foam materials are selected from the group consisting of polyurethane, polyethylene, and polystyrene. In addition, a possible advantageous material is cellulosic foam, and various cellulosic forms may be used. Other possible materials may be used in the new heat packs, and include pads of woven and non-woven forms of materials of the foregoing types. Thus, these may be loosely woven cellulosic material, such as that heretofore used for diapers, and various cloth materials. Combinations of such materials may also be used. Preferably, if foam is used, it may be open-celled foam, so that the aqueous salt solution can penetrate and be absorbed by the foam material and can retain the heat of the pack. The foam can be in the form of shredded foam or in several pieces; however a single, integrated piece of foam (e.g., so-called foam rubber material) is preferred, in that it better prevents saddlebagging when the pack is in use.

The invention and its attendant advantages are understood from the foregoing description and it is apparent that various changes may be made in the form, construction and arrangement of the parts without departing from the spirit and scope thereof or sacrificing its material advantages, the arrangements described being merely by way of example. The claims of the invention are not restricted to the specific forms shown.

I claim:

1. A trigger to initiate crystallization of a supercooled aqueous salt solution encased in a flexible container, comprising a puncturing means, salt crystals and a sealing means, the puncturing means being attached by a sealing means to the exterior of the flexible container, the trigger, when activated, being configured for puncturing the flexible container for allowing the supercooled aqueous salt solution to contact the salt crystals, thereby initiating crystallization, and the sealing means prevents any leakage of the solution from the container when the flexible container is punctured by the trigger.

2. The trigger of claim 1 wherein the salt of the supercooled aqueous salt solution is selected from the group consisting of sodium acetate, lead acetate, calcium nitrate tetrahydrate, sodium pyrophosphate and sodium thiosulfate.

3. The trigger of claim 1 wherein the flexible container composes materials selected from the group consisting of rubber, vinyl, vinyl coated fabric, nylon polylaminate and polyethylene.

4. The trigger of claim 1 wherein the puncturing means comprises a base plate with a plurality of piercing members.

5. The trigger of claim 4 wherein the sealing means is a contact adhesive seal having a diameter greater than that of the base plate.

6. The trigger of claim 1 wherein the puncturing means is on the opposite side of the flexible container as the salt crystals, and is activated when the puncturing means punctures both sides of the flexible container, allowing the salt solution to contact the salt crystals.

7. The trigger of claim 1 wherein the puncturing means is on both sides of the flexible container, and the salt crystals are deposited on the puncturing means.

8. A trigger to initiate crystallization of a supercooled aqueous salt solution encased in a flexible container, comprising a puncturing means, salt crystals and a sealing means, the puncturing means being attached by a sealing means to the exterior of the flexible container, the trigger, when activated, puncturing the flexible container to allow the supercooled aqueous salt solution to contact the salt crystals, thereby initiating crystallization, wherein the sealing means prevents any leakage of the solution from the container when the container is punctured by the trigger, the salt of the supercooled aqueous salt solution being selected from the group consisting of sodium acetate, lead acetate, calcium nitrate tetrahydrate, sodium pyrophosphate and sodium thiosulfate, the flexible container comprising material selected from the group consisting of rubber, vinyl, vinyl coated fabric, nylon polylaminate and polyethylene, the puncturing means comprising a base plate with a plurality of piercing members, and the sealing means is comprising a contact adhesive seal having a diameter greater than that of the base plate.

9. A heat pack comprising a flexible container having a trigger to initiate crystallization of a supercooled aqueous salt solution encased in the flexible container, thereby releasing heat, the trigger comprising a puncturing means, salt crystals and a sealing means, the trigger being attached by a sealing means to the exterior of the flexible container, the trigger, when activated, puncturing a surface of flexible container for causing the supercooled aqueous salt solution to contact the salt crystals, thereby initiating crystallization, and wherein the sealing means prevents any leakage of the solution from the container when punctured by the trigger.

10. The heat pack of claim 9 wherein attached to the exterior of the flexible container is a fastening means to secure the heat pack to a body part.

11. The heat pack of claim 10 wherein the fastening means is a strap which is attached using a contact adhesive.

12. The heat pack of claim 9 wherein affixed to the exterior of the heat pack is a liquid crystal temperature indicator.

13. The heat pack of claim 9 wherein the salt of the supercooled aqueous salt solution is selected from the group consisting of sodium acetate, lead acetate, calcium nitrate tetrahydrate, sodium pyrophosphate and sodium thiosulfate, the flexible container comprising material selected from the group consisting of rubber, vinyl, vinyl coated fabric, nylon polylaminate and polyethylene, the puncturing means comprising a base plate with a plurality of piercing members, and the sealing means comprising contact adhesive seal having a diameter greater than that of the base plate.

14. The heat pack of claim 9 wherein the flexible container encloses a flexible foam pad immersed in the salt solution.

15. The heat pack of claim 14 wherein the flexible foam pad is one piece.

16. The heat pack of claim 14 wherein the flexible foam pad is of material selected from the group consisting of polyurethane, polyethylene, polystyrene, and cellulose.

17. The heat pack of claim 9 wherein the puncturing means is on both sides of the flexible container, and the salt crystals are deposited on the puncturing means.

\* \* \* \* \*